United States Patent
Pettini et al.

(10) Patent No.: US 10,780,258 B2
(45) Date of Patent: Sep. 22, 2020

(54) THERMIC INFUSION SYSTEM

(71) Applicant: Life Warmer Inc., Canton, CT (US)

(72) Inventors: John Robert Pettini, Canton, CT (US); Charles John Tepper, Carrolton, TX (US); Richard Ray Thomson, Dallas, TX (US); James Kevin McCoy, Garland, TX (US); Jeffrey Alan Garrett, Allen, TX (US)

(73) Assignee: Life Warmer Inc., Canton, CT (US)

( * ) Notice: Subject to any disclaimer, the term of this patent is extended or adjusted under 35 U.S.C. 154(b) by 0 days.

(21) Appl. No.: 15/557,006

(22) PCT Filed: Mar. 10, 2016

(86) PCT No.: PCT/US2016/021795
§ 371 (c)(1),
(2) Date: Sep. 8, 2017

(87) PCT Pub. No.: WO2016/145211
PCT Pub. Date: Sep. 15, 2016

(65) Prior Publication Data
US 2018/0064921 A1    Mar. 8, 2018

Related U.S. Application Data

(60) Provisional application No. 62/131,237, filed on Mar. 10, 2015.

(51) Int. Cl.
*A61M 39/08*    (2006.01)
*A61M 5/44*    (2006.01)
*A61M 1/36*    (2006.01)

(52) U.S. Cl.
CPC ............ *A61M 39/08* (2013.01); *A61M 1/369* (2013.01); *A61M 5/44* (2013.01); *A61M 2205/36* (2013.01)

(58) Field of Classification Search
CPC .... A61M 1/369; A61M 5/44; A61M 2205/36; A61M 2205/3653; A61M 2205/3673;
(Continued)

(56) References Cited

U.S. PATENT DOCUMENTS 1,995,302 A * 3/1935 Goldstein ............... A61M 5/44
                                                              392/470
2,063,902 A    12/1936 Beasley
(Continued)

FOREIGN PATENT DOCUMENTS

DE    102007056169 A1    5/2009
DE    10211004481 A1    2/2011
(Continued)

OTHER PUBLICATIONS

Ku, David N. "Blood Flow in Arteries". Annu. Rev. Fluid. Mech. 1997. 29:399-434. (Year: 1997).*
(Continued)

*Primary Examiner* — Kami A Bosworth
(74) *Attorney, Agent, or Firm* — Robert H. Frantz

(57) ABSTRACT

A thermic infusion system includes a thermal tubing system and a control system. The thermal tubing system has a tubal body with at least one tubal segment. The tubal segment includes a thermal element that may receive energy, such as electrical energy, to increase temperature within the tubal body. The control system may regulate the amount of energy received by the tubal segment using one or more sensors positioned within the tubal body.

17 Claims, 10 Drawing Sheets

(58) Field of Classification Search
CPC .......... A61M 39/08; A61M 2205/3606; A61M 2205/3633; A61M 2206/10–22
See application file for complete search history.

(56) References Cited

U.S. PATENT DOCUMENTS

| | | | | |
|---|---|---|---|---|
| 2,087,586 | A | 7/1937 | Tishman | |
| 2,102,523 | A | 12/1937 | Ferrara | |
| 2,274,839 | A * | 3/1942 | Marick | F16L 53/38 219/522 |
| 2,357,238 | A | 8/1944 | Trimble | |
| 3,064,649 | A | 11/1962 | Lee | |
| 3,140,716 | A | 7/1964 | Harrison | |
| 3,275,802 | A | 9/1966 | Vandivere | |
| 3,315,681 | A | 4/1967 | Poppendiek | |
| 3,370,153 | A | 2/1968 | Fresne | |
| 3,425,415 | A | 2/1969 | Gordon | |
| 3,475,590 | A | 10/1969 | Pins | |
| 3,485,245 | A | 12/1969 | Lahr | |
| 3,518,393 | A | 6/1970 | Besselling | |
| 3,551,641 | A | 12/1970 | Truhan | |
| 3,553,429 | A | 1/1971 | Nelson | |
| 3,590,215 | A | 6/1971 | Anderson | |
| 3,614,385 | A | 10/1971 | Horstman | |
| 3,768,977 | A | 10/1973 | Brumfield | |
| 3,908,652 | A | 9/1975 | Weissinger | |
| 3,976,129 | A | 8/1976 | Silver | |
| 4,038,519 | A * | 7/1977 | Foucras | A61M 1/369 392/472 |
| 4,167,663 | A | 10/1979 | Granzow, Jr. et al. | |
| 4,177,816 | A | 12/1979 | Torgeson | |
| 4,293,762 | A | 10/1981 | Ogawa | |
| 4,314,143 | A | 2/1982 | Bilstad | |
| 4,358,664 | A | 11/1982 | Kronseder | |
| 4,532,414 | A | 7/1985 | Shah | |
| 4,553,023 | A * | 11/1985 | Jameson | F16L 53/38 392/472 |
| 4,574,876 | A | 3/1986 | Aid | |
| 4,623,333 | A | 11/1986 | Fried | |
| 4,678,460 | A | 7/1987 | Rosner | |
| 4,707,587 | A | 11/1987 | Greenblatt | |
| 4,709,698 | A * | 12/1987 | Johnston | A61B 18/08 604/114 |
| 4,735,609 | A | 4/1988 | Comeau | |
| 4,759,749 | A | 7/1988 | Verkaart | |
| 4,782,212 | A | 11/1988 | Bakke | |
| 4,801,777 | A | 1/1989 | Auerbach | |
| 5,063,994 | A | 11/1991 | Verkaart | |
| 5,097,898 | A | 3/1992 | Verkaart | |
| 5,108,372 | A | 4/1992 | Swenson | |
| 5,125,069 | A | 6/1992 | O'Boyle | |
| 5,250,032 | A | 10/1993 | Carter | |
| 5,254,090 | A * | 10/1993 | Lombardi | A61M 25/0009 600/18 |
| 5,254,094 | A | 10/1993 | Starkey | |
| 5,381,510 | A | 1/1995 | Ford | |
| 5,381,511 | A * | 1/1995 | Bahar | F16L 11/12 392/472 |
| 5,514,095 | A * | 5/1996 | Brightbill | A61M 5/44 604/113 |
| 5,862,303 | A * | 1/1999 | Adar | F16L 47/03 148/403 |
| 5,875,282 | A | 2/1999 | Jordan | |
| 6,142,974 | A | 11/2000 | Kistner | |
| 6,641,556 | B1 * | 11/2003 | Shigezawa | A61M 5/44 604/113 |
| 6,746,439 | B2 | 6/2004 | Lenker | A61M 5/44 604/500 |
| 7,158,719 | B2 | 1/2007 | Cassidy | |
| 7,741,815 | B2 | 6/2010 | Cassidy | |
| 8,078,040 | B2 * | 12/2011 | Forrester | A61M 16/0875 392/481 |
| 8,150,244 | B2 | 4/2012 | Cassidy | |
| 8,380,056 | B2 * | 2/2013 | Evans | F24H 1/142 392/465 |
| 8,559,800 | B2 * | 10/2013 | Ellis | F16L 53/37 392/468 |
| 8,660,415 | B2 | 2/2014 | Cassidy | |
| 8,690,842 | B2 | 4/2014 | Lopez | |
| 2001/0011585 | A1 | 8/2001 | Cassidy | |
| 2002/0120314 | A1 * | 8/2002 | Evans | A61F 7/12 607/96 |
| 2003/0114795 | A1 | 6/2003 | Faries, Jr. et al. | |
| 2006/0020255 | A1 * | 1/2006 | Cassidy | A61M 5/1411 604/500 |
| 2006/0150792 | A1 | 7/2006 | Cazzini | |
| 2007/0142773 | A1 * | 6/2007 | Rosiello | A61F 7/0085 604/113 |
| 2008/0234619 | A1 | 9/2008 | Fausset et al. | |
| 2009/0319011 | A1 | 12/2009 | Rosiello | |
| 2010/0025328 | A1 | 2/2010 | Davies et al. | |
| 2010/0059498 | A1 | 3/2010 | Hansen | |
| 2011/0098642 | A1 | 4/2011 | Cassidy | |
| 2011/0202034 | A1 | 8/2011 | Lopez | |
| 2013/0112201 | A1 * | 5/2013 | Graham | A61M 16/0875 128/203.27 |
| 2013/0152931 | A1 * | 6/2013 | Sims | F16L 53/38 128/204.17 |
| 2014/0169775 | A1 | 6/2014 | Cassidy | |
| 2014/0276587 | A1 * | 9/2014 | Imran | A61M 5/1483 604/506 |
| 2015/0020803 | A1 * | 1/2015 | Dunlop | A61M 16/01 128/203.14 |
| 2017/0000973 | A1 * | 1/2017 | Otake | A61M 25/005 |
| 2018/0064921 | A1 | 3/2018 | Pettini | |

FOREIGN PATENT DOCUMENTS

| | | |
|---|---|---|
| EP | 1462137 B1 | 12/2006 |
| WO | 0002608 A1 | 1/2000 |
| WO | 0107109 A1 | 2/2001 |
| WO | 2011137266 A1 | 11/2011 |
| WO | 2014118313 A1 | 7/2014 |

OTHER PUBLICATIONS

Thermal Angel; "Thermal Angel (TA-200)" retrieved on Oct. 28, 2014 from http://www.thermalangel.com.

Thermal Angel; "Comparison", retrieved on Oct. 28, 2014 from http://www.thermalangel.com.

Gaymar Ind.; "Medi-Temp III Ref FW600 Blood/Fluid Warmer"; retrieved on Oct. 15, 2019 from http://techweb.stryker.com.

Smiths Medical; "Operator's Manual: Level 1 Hotline Blood and Fluid Warmer", retrieved on Oct. 15, 2019 from http://www.smitsmedical.com.

Ecourses; "Ch. 4 Beam Stresses", retrieved on Mar. 15, 2019 from http://www.ecourses.ou.edu.

Ge; "enFlow IV Fluid/Blood Warmer", copyright 2009.

Dubick, et al; "Evaluation of Commercially Available Fluid-Warming Devices for Use in Forward Surgical and Combat Areas"; Military Medicine, vol. 170, Jan. 2005.

Arizant Healthcare; "Ranger Operator's Manual: Model 245 SmartHeat*", copyright 2009.

European Patent Office; "Communication prusuant to Article 94(3) EPC"; dated May 12, 2020 in related PCT/EPO patent application No. 16 712 595.4-1122.

Patent Translate; "Description DE102011004481A1"; machine translated description from Item #1 Stihler Electronic GmbH listed in the Foreign Patent Documents section of this IDS.

Patent Translate; "Description DE102007056169A1"; machine translated description from Item #2 Volker listed in the Foreign Patent Documents section of this IDS.

* cited by examiner

FIG. 11B   TEMPERATURE MEASUREMENT
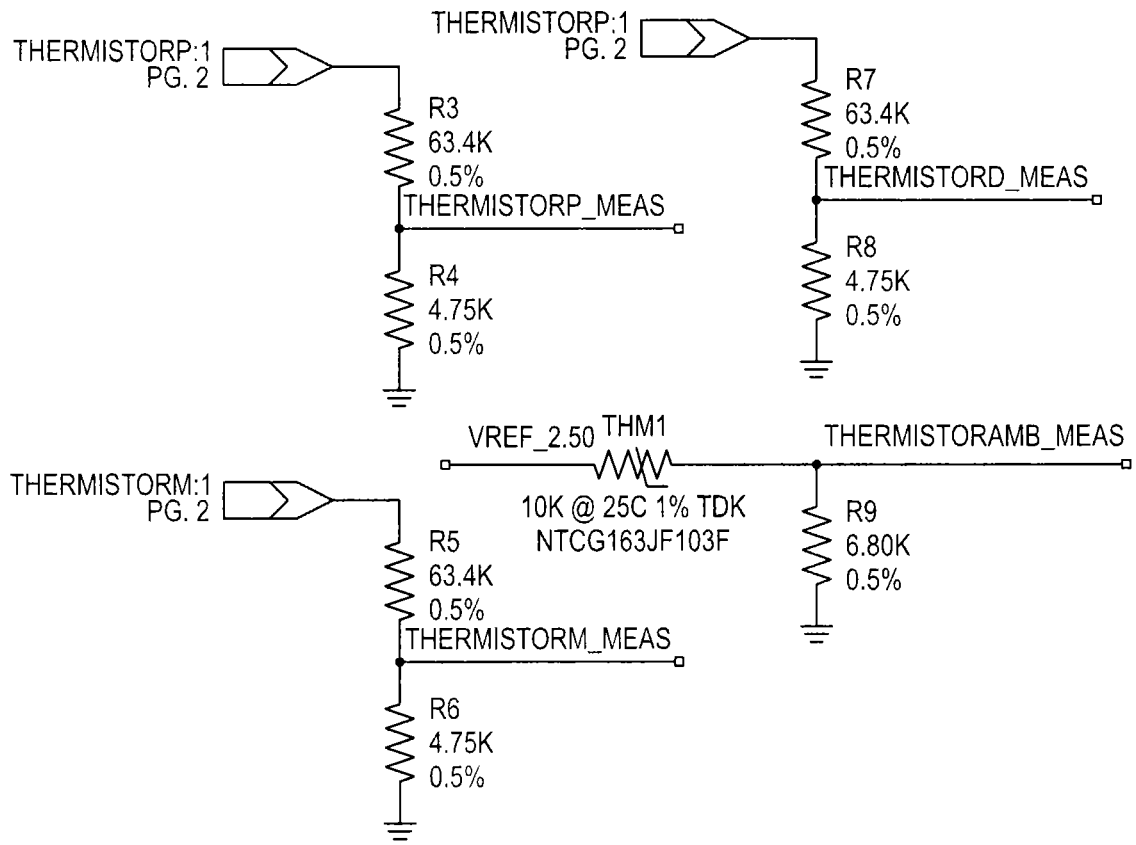
FIG. 11C   BATTERY MEASUREMENT
$$V_{IN} = [(210K + 10.5K) * V_{REF} * ADC] / [2^{12} * 10.5K]$$
$$= ADC * 0.012817383 \ (V)$$
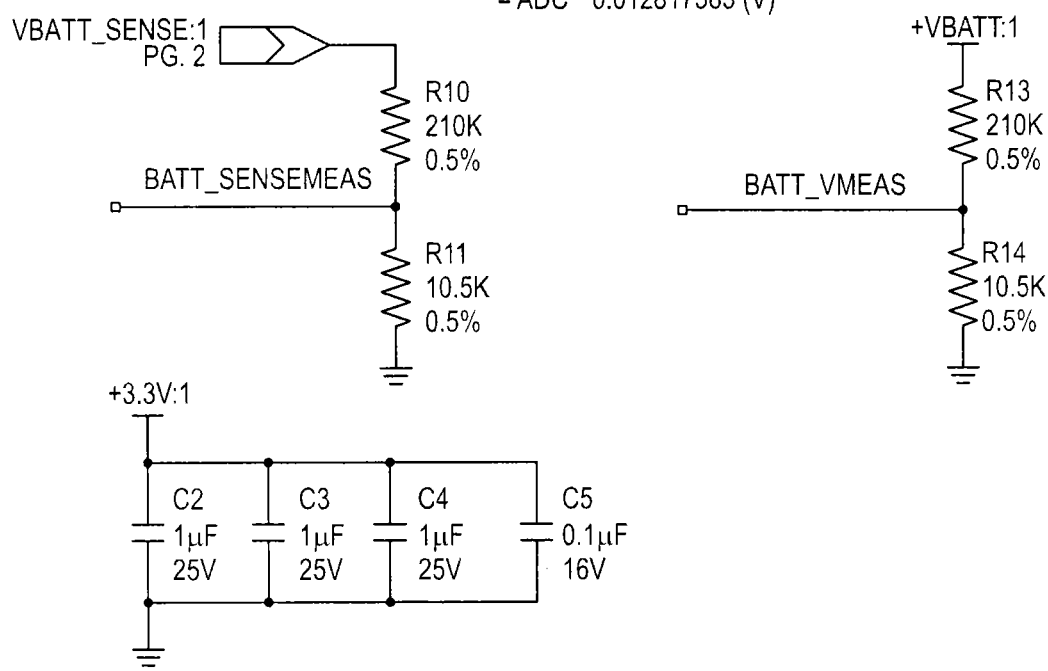

THERMIC INFUSION SYSTEM

CROSS REFERENCE TO RELATED APPLICATIONS

This application is a U.S. National Stage application filed under 35 U.S.C. § 371 of International Application No. PCT/US16/21795, filed Mar. 10, 2016, which claims priority under 35 U.S.C. § 119(e) from provisional application No. 62/196,881, filed Mar. 10, 2015. The entire contents of the above-referenced patent applications are hereby expressly incorporated herein by reference in their entirety.

BACKGROUND

Hypothermia occurs when the body's core temperature drops below 35 degrees Celsius due to extreme exposure to cold, decrease in heat production, or increase in heat loss. It is a generally understood physiological fact that nearly one hundred percent of all trauma patients that reach a core temperature of 32 degrees Celsius or less will die. Trauma patients also generally cool quickly due to a number of factors, and such cooling leads to what is known as the "triad of death": hypothermia, acidosis, coagulopathy.

Warming of intravenous fluid (e.g., blood) is a critical early intervention technique that may decrease mortality and morbidity related events due to hypothermia. By providing a patient with warmed blood or other resuscitative fluids through an intravenous device, a more favorable prognosis may be achieved.

Portability of the intravenous device may further aid in the early prevention of hypothermia—i.e., the trauma patient is provided with warmed fluid at the scene of the trauma and in a more immediate manner. Currently within the art, infusion fluid heaters primarily use a serpentine path between heating elements, flow into a rectangular geometry cartridge space expanding surface area contact with a heating element, and/or provide heating elements within a bath of fluid. These devices are bulky, cumbersome, and require multiple components and are challenging to set up. As such, portability of the infusion fluid heaters within the field is limited.

In warming blood, hemolysis also becomes a concern as the blood must remain below a certain temperature in order to prevent hemolysis. As flow through intravenous devices is generally laminar, blood positioned near the inner wall of the intravenous device may reach the temperature of the inner wall. Placement of a heating element in contact with the inner wall raises hemolysis concerns and has generally been avoided in the art. Even further, current inline blood warmers within the art typically place shear forces on a fluid as the fluid flows from infusion tubing into a cartridge and outflows via a tubing to the patient. Additionally, the flow dynamics change from laminar to transitional and turbulent during this process. Increased shear forces and non-laminar flow is known to damage membranes of red blood cells affecting distensibility and impairing the function of transfused blood to oxygenate tissue in the microcirculation.

Therefore, there is a need in the art for new and improved laminar flow infusion systems that can safely regulate the temperature of fluid while providing portability of the device within the field.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIGS. 11A-11D illustrate schematic circuit diagrams of an exemplary control system for use in the in thermic infusion system of FIG. 1A.

DETAILED DESCRIPTION OF EXEMPLARY EMBODIMENTS

Figure 1A:
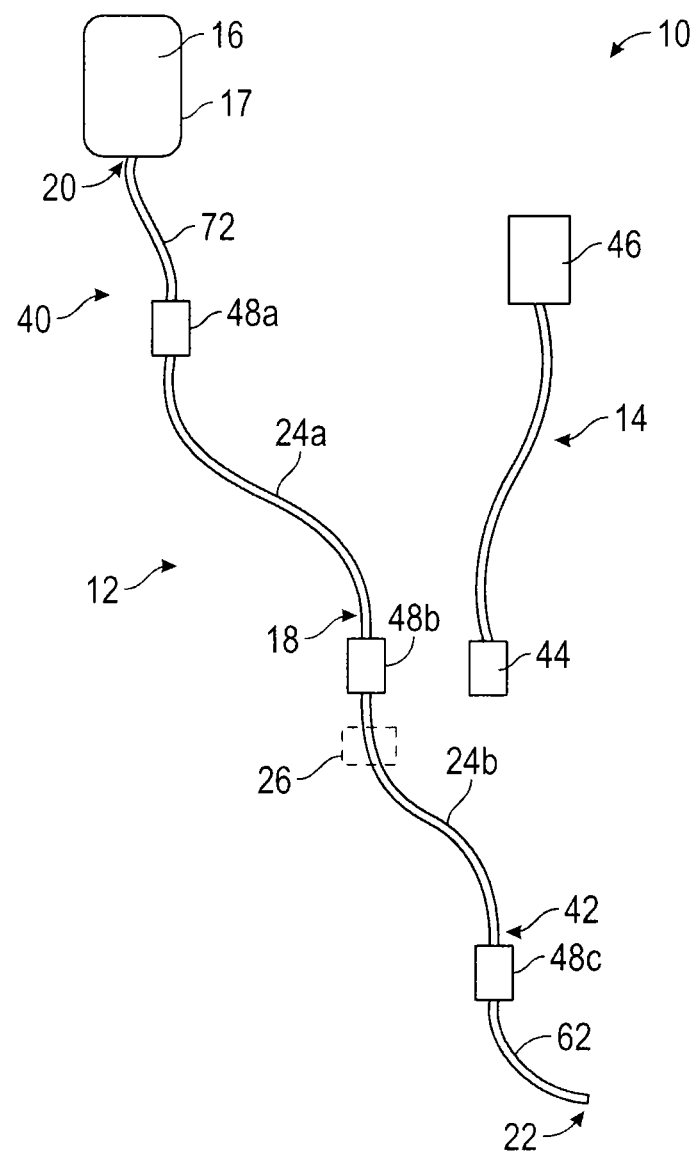
FIG. 1A is a diagrammatic view of a thermic infusion system constructed in accordance with the present disclosure.

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail in order to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAAB-CCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including but not limited to each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

As used herein, the term "patient" is meant to include all organisms, whether alive or dead. For example, a method according to the inventive concepts disclosed herein may be used to regulate fluid temperature for infusion into a living human, horse, cow, sheep, cat, dog, and the like. In another example, a method according to the inventive concepts disclosed herein may be used in a non-living organism to train medical personnel, for example.

Although the following disclosure relates to the medical field, the thermic infusion device using different dimensions and optimizations may be used to efficiently heat and/or cool flowing fluid or gas to a safe operating temperature, over a range of flow rates. For example, applicable industry uses may include, petrochemical, chemical processing, pharmaceutical processing, food processing and the like.

Certain exemplary embodiments of the invention will now be described with reference to the drawings. In general, such embodiments relate to thermic infusion systems and methods.

Referring to FIG. 1A, a thermic infusion system 10 is illustrated. Generally, the thermic infusion system 10 includes a thermal tubing system 12 and a control system 14. The thermic infusion system 10 may generally aid in controlling the temperature of an infusion fluid, such as infusion fluid 16 which may be, by way of illustration and not by limitation, blood, plasma, or other infusates. For example, in some embodiments, controlling the temperature of the infusion fluid 16 may include controlling the temperature of the infusion fluid 16 to a physiological beneficial temperature range (e.g., between approximately 35-39 degrees Celsius). In some embodiments, controlling the temperature of the infusion fluid 16 may include controlling the temperature of the infusion fluid 16 to a pre-set temperature range (e.g., between approximately 37-41 degrees Celsius). In some embodiments, controlling the temperature of the infusion fluid 16 may include controlling the temperature of the infusion fluid 16 over a range of flow rates (e.g., 2-50 mL/min) and/or ambient conditions. In some embodiments, the thermic infusion system 10 may maintain fluid below a potentially detrimental temperature (e.g., temperature wherein hemolysis occurs), for example.

Referring to the thermal tubing system 12 shown in FIG. 1A, controlling the temperature range of the infusion fluid 16 may include using heating and/or cooling elements embedded in or contacting the thermal tubing system 12. In some embodiments, the thermal tubing system 12 may substitute for a standard infusion line as known by one skilled in the art.

Figure 1B:
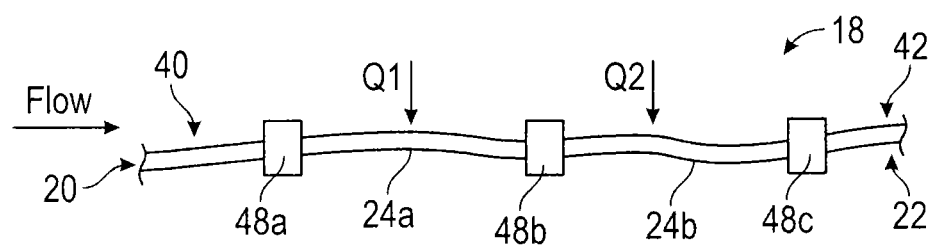
FIG. 1B is a diagrammatic view of heat transfer through the thermic infusion system illustrated in FIG. 1A.
Figure 2:
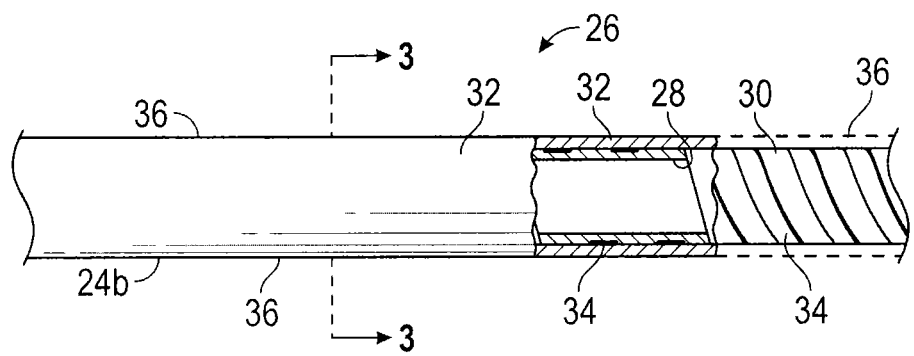
FIG. 2 is an exemplary embodiment of a portion of a tubal segment for use in the thermic infusion system of FIG. 1A. A portion of the tubal segment is illustrated in a cross sectional view and a portion of the tubal segment is illustrated with an outer sheath of the tubal segment removed such that a thermal element of the tubal segment is viewed.
Figure 3:
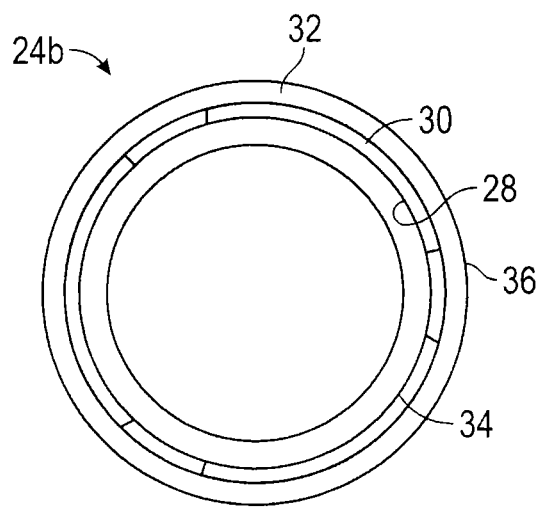
FIG. 3 is a cross sectional view of the tubal segment illustrated in FIG. 2 taken along line 3-3.

Referring to FIGS. 1-3, the thermal tubing system 12 includes a tubal body 18 having an inlet port 20 and an outlet port 22. The inlet port 20 may connect to a source 17 for the infusion fluid 16 such that fluid may flow into the inlet port 20 and through the tubal body 18 and out of the outlet port 22 to a patient. For example, the source 17 of the infusion fluid 16 may be an infusion bag as is known within the art. In some embodiments, elements such as a drip chamber, injection port, roller clamp, slide clamp, and/or the like may be positioned adjacent to the inlet port 20, tubal body 18, and/or source 17 of the infusion fluid 16. Such elements are well known to a person skilled within the art and need no further description herein. The outlet port 22 may connect to a cannula, and/or the like for insertion into the patient such that the infusate may flow to the patient. In some embodiments, the tubal body 18 may be disposable.

In some embodiments, the tubal body 18 may be configured such that there is limited or no change in the geometry therethrough. For example, in some embodiments, the tubal body 18 may be configured to be at a substantially similar diameter therethrough. Such limited change in the geometry may provide for laminar flow of the infusion fluid 16 through the tubal body 18.

The flow pattern of the infusion fluid 16 through the thermal tubing system 12 may be laminar and occur at a Reynolds Number (Re) below 2000, known as the critical number. For example, the Re may be approximately 300 to 600. As such, in some embodiments, flow conditions of the infusion fluid 16 through substantially all of the thermal tubing system 12 may result in a Reynolds number no greater than 1000. In some embodiments, flow conditions of the infusion fluid 16 through substantially all of the thermal tubing system 12 may result in a Reynolds number no greater than 750. In some embodiments, flow conditions of the infusion fluid 16 through substantially all of the thermal tubing system 12 may result in a Reynolds number no greater than 600. In some embodiments, flow conditions of the infusion fluid 16 through substantially all of the thermal tubing system 12 may result in a Reynolds number no greater than 500. In some embodiments, flow conditions of the infusion fluid 16 through substantially all of the thermal tubing system 12 may result in a Reynolds number no greater than 400. In some embodiments, flow conditions of the infusion fluid 16 through substantially all of the thermal tubing system 12 may result in a Reynolds number no greater than 350.

Additionally, configuration of the thermal tubing system 12 may be such that calculated shear force of the thermal tubing system 12 associated with infusion fluid 16 flowing therethrough is less than maximum physiological shear stress within the human vascular system (i.e., 10 Pa). For example, in some embodiments, the calculated shear force may be between approximately 4 Pa to 9 Pa. In some embodiments, the calculated shear force through substantially all of the thermal tubing system 12 may be less than 9 Pa. In some embodiments, the calculated shear force through substantially all of the thermal tubing system may be less than 8 Pa. In some embodiments, the calculated shear force through substantially all of the thermal tubing system may be less than 7 Pa. In some embodiments, the calculated shear force through substantially all of the thermal tubing system may be less than 6 Pa. In some embodiments, the calculated shear force through substantially all of the thermal tubing system may be less than 5 Pa. In some embodiments, the calculated shear force through substantially all of the thermal tubing system may be less than 5.5 Pa.

The tubal body 18 may include one or more tubal segments 24. For example, FIG. 1A illustrates the tubal body 18 having two tubal segments 24a and 24b. Each tubal segment 24a and 24b may have similar or different lengths. Any number of tubal segments 24 may be included within the tubal body 18. Each tubal segment 24a and 24b may provide heat transfer (e.g., heating/cooling) to the infusion fluid 16 flowing through the tubal body 18. Generally, formation of the tubal segments 24 are such that electrical energy may be converted for heat transfer (e.g., heating, cooling), such that the temperature of the infusion fluid 16 may be affected (e.g., raised, lowered, stabilized).

FIG. 2 illustrates a portion 26 of the tubal segment 24b of FIG. 1A. For simplicity in description, the tubal segment 24b is described in further detail here; however, it should be appreciated by one skilled in the art that the tubal segment 24a may contain the same elements described in relation to tubal segment 24b.

Generally, the tubal segment 24b may be configured to provide thermal transfer of heat (e.g., heating/cooling) to the infusion fluid 16. In some embodiments, the tubal segment 24b may provide the feel and/or handling characteristics of conventional intravenous (IV) tubing known within the art. In some embodiments, the tubal segment 24b may be configured to be resistant to kinking when coiled for packaging and/or when handled in use. In some embodiments, if a kink in the tubal segment 24b occurs, the tubal segment 24b may rebound from such kink. In some embodiments, the tubal segment 24b may provide visibility of the fluid path of the infusion fluid 16 through the tubal body 18. As a person skilled in art is aware, in patient care settings, standard infusion tubing routinely kinks and is crushed. The tubal body 18, and in particular the tubal segments 24a and 24b may configured to be kink resistant and crush resistant as described in further detail herein.

Referring to FIGS. 1-4, the tubal segment 24b, as also applied to the tubal segment 24a, includes an inner sheath 28, a thermal element 30, and an outer sheath 32. In some embodiments, the inner sheath 28 may be formed of more rigid material(s) as compared to the outer sheath 32 such that kinking and/or crushing of the tubal segment 24b may be reduced and/or prevented. Additionally, the materials selected for the inner sheath 28 and/or the outer sheath 32 may be configured such that rebound may occur in a kinking and/or crushing event. During rebound, it should be noted that flow of the fluid through the tubal body 18 may continue and not be impeded. In some embodiments, the ratio of thickness of the inner sheath 28 as compared to the outer sheath 32 may be configured such that kinking and/or crushing of the tubal segment 24b may be reduced and/or prevented, and/or rebound after a kinking and/or crushing event may occur. For example, the inner sheath 28 may have a thickness of approximately 0.15 mm and the outer sheath 32 may have a thickness of approximately 0.39 mm.

The inner sheath 28 may be configured as a hollow cylindrical body for conveying infusion fluid 16 therethrough. The inner sheath 28 may be formed of any flexible, biocompatible material including, but not limited to, one or more extrudable polymers, polyurethane, one or more thermoplastic elastomers, Elastollan, fluorinated ethylene propylene (FEP) and/or the like, for example. Generally, the material of the inner sheath 28 may provide for heat transfer from the thermal element 30 to the infusion fluid 16 traveling through the tubal body 18. In some embodiments, the inner sheath 28 may be formed of a completely or intermittently clear (e.g., translucent, transparent, or the like) material. In some embodiments, the inner sheath 28 may be formed of a completely or intermittently opaque material.

In some embodiments, a tie layer 34 may optionally be positioned between the inner sheath 28 and the thermal element 30. The tie layer 34 may be a thin layer configured to stabilize the thermal element 30. The tie layer 34 may be formed of any flexible, biocompatible material, including, but limited to, polyvinyl chloride (PVC), polyurethane, Pellethane, Pebax, and/or the like, for example. In some embodiments, the tie layer 34 may be used to prevent slippage of the thermal element 30 during handling. In some embodiments, the tie layer 34 may be formed of clear (e.g., transparent, translucent, and/or the like) material.

The thermal element 30 is configured to convert energy (e.g., electrical energy) into heat to propagate heat transfer (e.g., cooling or heating) to the infusion fluid 16. For example, heat from the thermal element 30 may be transferred through the inner sheath 28 and the tie layer 34 to the infusion fluid 16 flowing through the tubal segment 24b. In some embodiments, the thermal element 30 may be formed of conductive materials including, but not limited to, copper, nickel, cuprothol, silver, gold aluminum, molybdenum, tungsten, zinc, palladium, nichrome, other suitable alloys, and/or the like, for example. In some embodiments, the thermal element 30 may be formed of a plurality of materials woven into a ribbon formation, solid circular wire, ribbon with a substantially rectangular cross section, and/or any other cross sectional configuration (e.g., fanciful). In some embodiments, the thermal element 30 may be formed of a flexible Peltier element, or other element such that the thermal element 30 may both heat and cool the infusion fluid 16 flowing through the tubal segment 24b.

The thermal element 30 may be positioned adjacent to the inner sheath 28 or the tie layer 34. In some embodiments, the thermal element 30 may extend the entire length of the tubal segment 24b. In some embodiments, the thermal element 30 may extend a portion of the tubal segment 24b.

Figure 4:
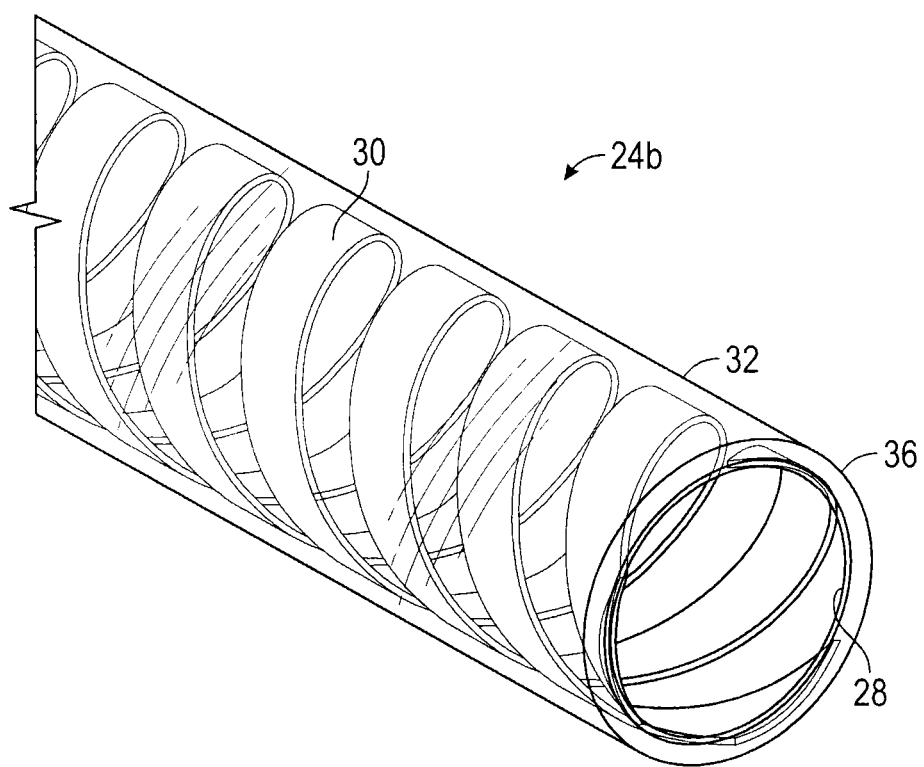
FIG. 4 is a perspective view of an exemplary tubal segment for use in the thermic infusion system of FIG. 1A.

In some embodiments, the thermal element 30 may cover the entire inner sheath 28. In some embodiments, the thermal element 30 may cover a portion of the inner sheath 28. For example, as illustrated in FIGS. 2 and 4, in some embodiments, the thermal element 30 may be provide in a helical-type configuration (e.g., single helix, double helix, triple helix, and/or the like) around the inner sheath 28 and tie layer 34 covering a portion of the inner sheath 28. For example, in some embodiments, the thermal element 30 may be configured as a triple helix formed as a ribbon of cuprothol and/or silver plated copper wire. In another example, the thermal element 30 may be configured as a double helix formed as a ribbon of nichrome.

Pitch of the thermal element 30 about the inner sheath 28 may be configured to reduce kinks, crushing, and/or aid in rebound of the tubal segment 24b. For example, in some embodiments, the pitch of the thermal element 30 about the inner sheath 28 may be approximately 6.3 mm/revolution.

In some embodiments, each tubal segment 24a and 24b may include differential energy transfer capabilities. For example, the tubal segment 24a positioned near the inlet port 20 may have greater energy transfer capabilities as compared to the tubal segment 24b positioned near the outlet port 22. As such, each tubal segment 24a and 24b may be formed of different materials and/or have different configurations such that differential energy transfer capabilities may be provided.

The outer sheath 32 may be formed of a material configured to reduce and/or prevent thermal energy loss. For example, the outer sheath 32 may be formed of a material configured to reduce and/or prevent thermal energy loss to an ambient environment. Such material may include, but is not limited to, polyurethane, Pellethane, and/or the like, for example. Additionally, in some embodiments, the material of the outer sheath 32 may be configured to electrically insulate the thermal element 30. The material of the outer sheath 32 may also be configured such that an outer surface 36 of the outer sheath 32 remains at a temperature well below that which produces any kind of burn. In some embodiments, the outer sheath 32 may be formed of completely or intermittently clear (e.g., translucent, transparent, or the like) material. In some embodiments, the outer sheath 32 may be formed of a completely or intermittently opaque material.

Referring to FIGS. 1-2, the control system 14 may modulate and/or regulate energy to the tubal segments 24a and 24b, and more particularly, to the thermal elements 30 of the tubal segments 24a and 24b. By modulating and/or regulating energy to the tubal segments 24a and 24b, temperature of the infusion fluid 16 may be controlled. FIGS. 11A-11D illustrate schematic diagrams of an exemplary control system 14a for use in the thermic infusion system of FIG. 1A. In some embodiments, the control system 14a may also include a temperature measurement system, a battery measurement system, and/or a status indicator system.

In some embodiments, each thermal element 30 of each tubal segment 24a and 24b may be controlled individually. As such, the control system 14 may be configured to control the temperature of the infusion fluid 16 flowing through the tubal body 18 by individually optimizing heat delivered through each tubal segment 24a and 24b. The thermic infusion system 10 may thus provide individually controlled tubal segments 24a and 24b configured to control fluid temperature of the infusate flowing therethrough to a predefined temperature (e.g., below hemolysis threshold).

Referring to FIG. 1B, in some embodiments, the control system 14 may provide a greater transfer of heat to the infusion fluid 16 flowing through the tubal segment 24a positioned at a proximal end 40 of the tubal body 18 as compared to the transfer of heat provided to the infusion fluid 16 flowing through the tubal segment 24b positioned at a distal end 42 of the tubal body 18. For example, a first amount of heat $Q_1$ may be provided to the tubal segment 24a and a second amount of heat $Q_2$ may be provided to the tubal segment 24b. The first amount of heat $Q_1$ may be greater than the second amount of heat $Q_2$ or, alternatively, the first amount of heat $Q_1$ may be less than the second amount of heat $Q_2$.

Figure 5:
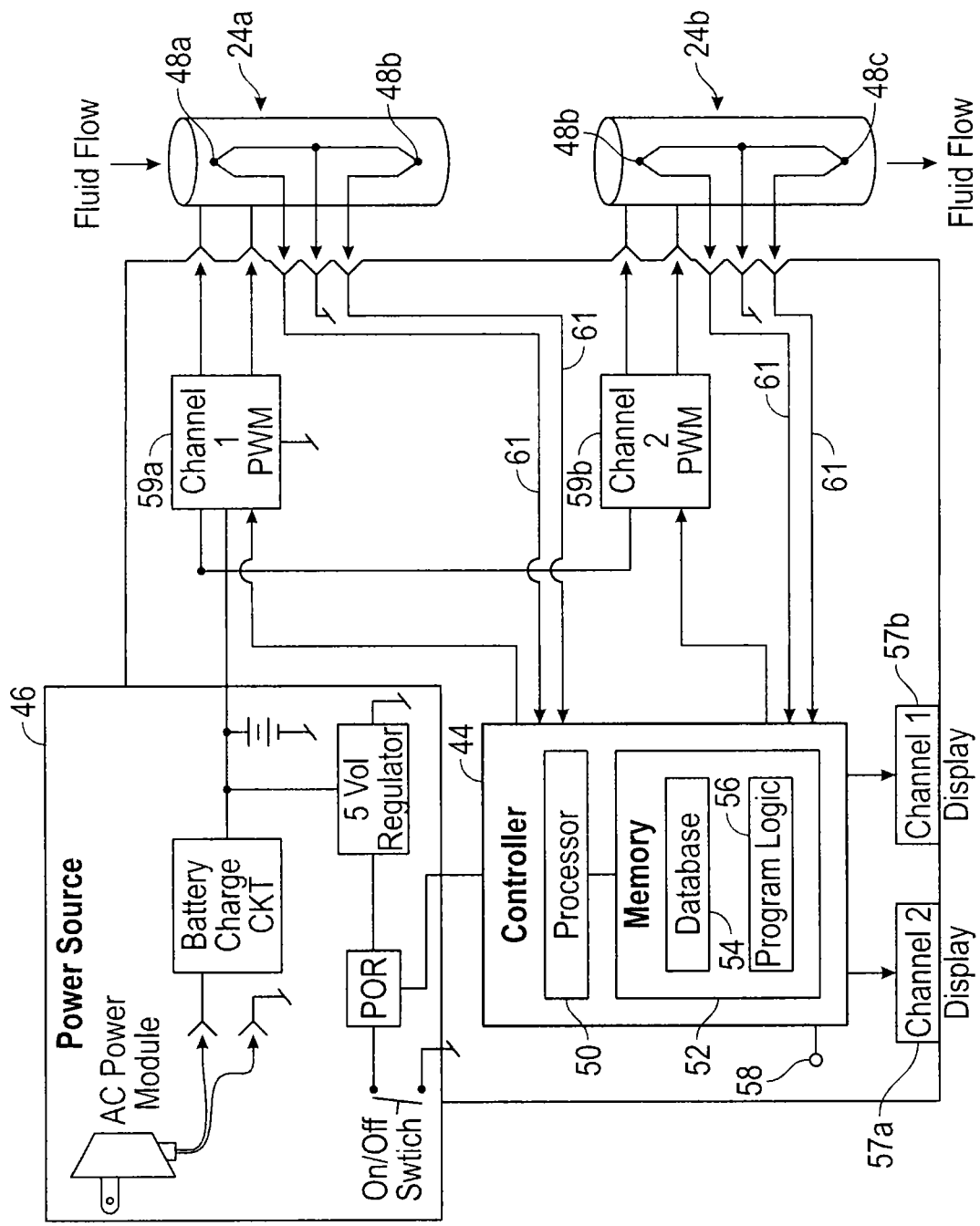
FIG. 5 is a block diagram of an exemplary control system and power supply for use in the thermic infusion system of FIG. 1A.

Referring to FIGS. 1, 2 and 5, the control system 14 may include a control unit 44, a power source 46, and one or more sensors 48. Generally, the control unit 44 may utilize data obtained by the one or more sensors 48 to determine the amount of heat Q to be provided to one or more tubal segments 24. In some embodiments, heat Q may be provided to the tubal segments 24 in the form of electrical energy supplied to the thermal elements 30. The one or more sensors 48 provide a signal to the control unit 44 indicative of the temperature of the infusion fluid 16 as it flows through the tubal body 18. The control unit 44 may utilize a control algorithm and data provided by the one or more sensors 48 to modulate energy (e.g., electrical energy) to the thermal elements 30 of the tubal segments 24a and 24b. In some embodiments, each thermal element 30 may be controlled individually.

In some embodiments, communication between the control unit 44 and multiple sensors 48 may provide a safety feedback control. For example, one or more sensors 48 may be positioned in communication with the infusion fluid 16 such that failure of one or more sensors 48 may provide a signal to the control unit 44. The control unit 44 may determine to continue operation, reduce operation or turn off. Such safety feedback control may maintain a safe fluid environment (e.g., temperature, flow).

The control unit 44 comprises one or more processors 50 capable of executing processor executable code and one or more non-transitory memory 52 capable of storing processor executable code. The processor executable code causes the processor 50 to receive data from the one or more sensors 48; analyze the data received from the sensors 48; and, provide electrical energy to the tubal segments 24a and 24b, and more particularly, to the thermal elements 30 of the tubal segments 24a and 24b based on the analysis of the data. Any suitable technique may be used to interpret the data received from the sensors 48. For example, the processor executable code may be configured to utilize techniques and/or algorithms known within the art (e.g., proportional/integral/derivative (PID) control, hierarchical (cascade) control, optimal (model predictive) control, intelligent (fuzzy logic) control, adaptive control, and/or the like).

The processor 50 may be implemented as a single processor or multiple processors working together to execute the logic described herein. Each processor 50 may be capable of reading and/or executing code and/or capable of creating, manipulating, retrieving, altering and/or storing data structure. Exemplary embodiments of the one or more processors 50 include, but are not limited to, digital signal processors (DSPs), central processing units (CPUs), field programmable gate arrays (FPGAs), microprocessors, multi-core processors, combinations thereof, and/or the like.

In some embodiments, the one or more processors 50 may be located remotely from one another and use a network protocol to communicate therebetween. To that end, in some embodiments, each element of the control unit 44 may be partially or completely network based, and may not be located in a single physical location (e.g., with a single housing). The network may permit uni-directional or bi-directional communication of information and/or data between the one or more processors 50 and/or the one or memories 52.

The one or more memories 52 may be capable of storing processor executable code and/or information including one or more databases 54 and program logic 56. For example, the database may store data indicative of sensing data provided by the one or more sensors 48. In some embodiments, the processor executable code may be stored as a data structure, such as a database and/or data table, for example. Additionally, the one or more memories 52 may be implemented as a conventional non-transient memory, such as, for example, random access memory (RAM), a CD-ROM, a hard drive, a solid state drive, a flash drive, a memory card, a DVD-ROM, an optical drive, combinations thereof, and/or the like.

The one or more memories 52 may be located in the same physical location as the one or more processors 50 (e.g., in a single housing), or located remotely from the one or more processors 50 and may communicate with the one or more processors 50 via a network, for example. Additionally, when more than one processor 50 is used, one or more memory 52 may be located in the same physical location as the processor 50, and one or more memory 52 may be located in a remote physical location from the processor 50. The physical location(s) of the one or more memories 52 may be varied. In some embodiments, the one or more memory 52 may be implemented as a "cloud" memory" (i.e., one or more memory may be partially, or completely accessed using a network).

Figure 11A:
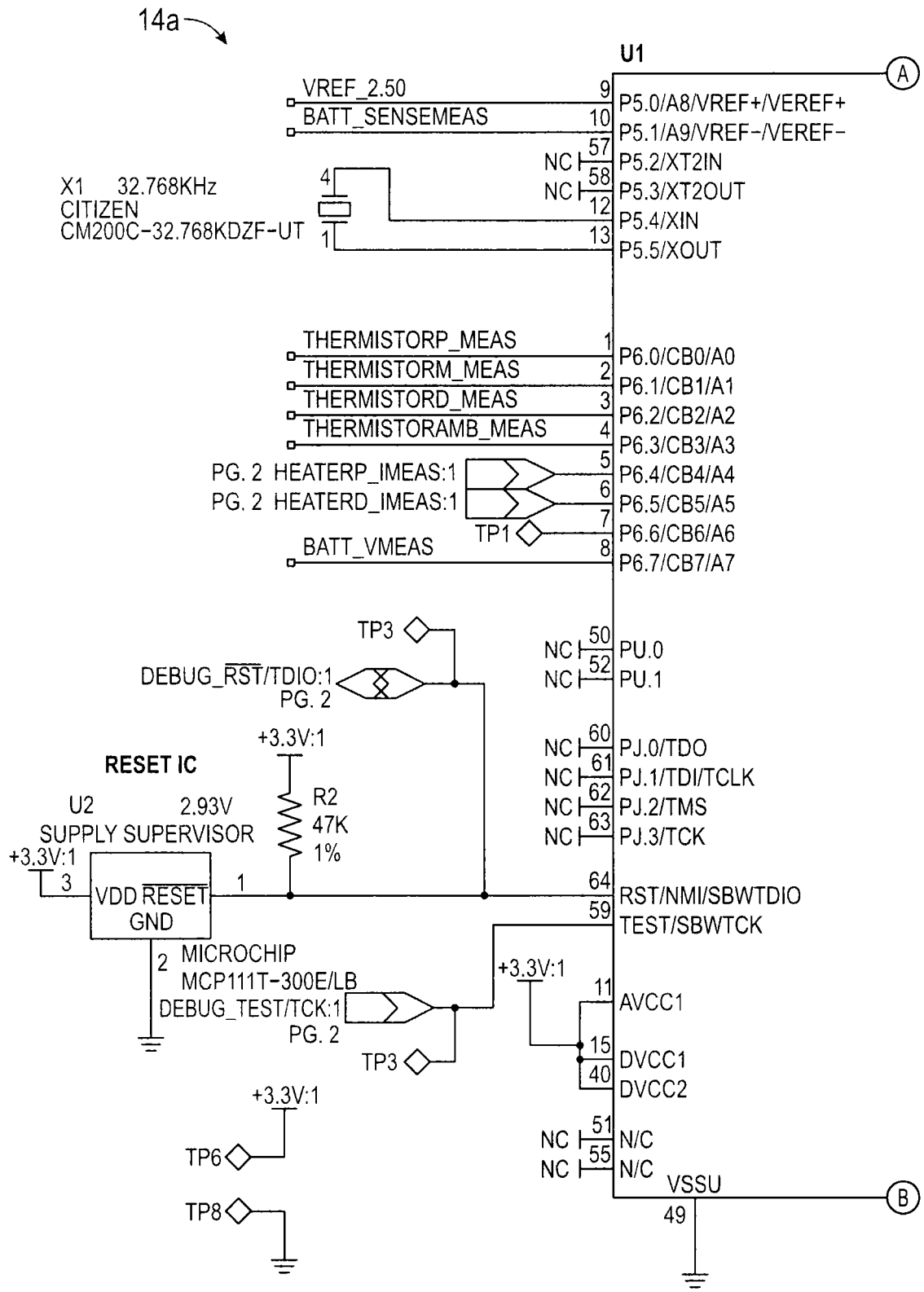
Figure 11A:
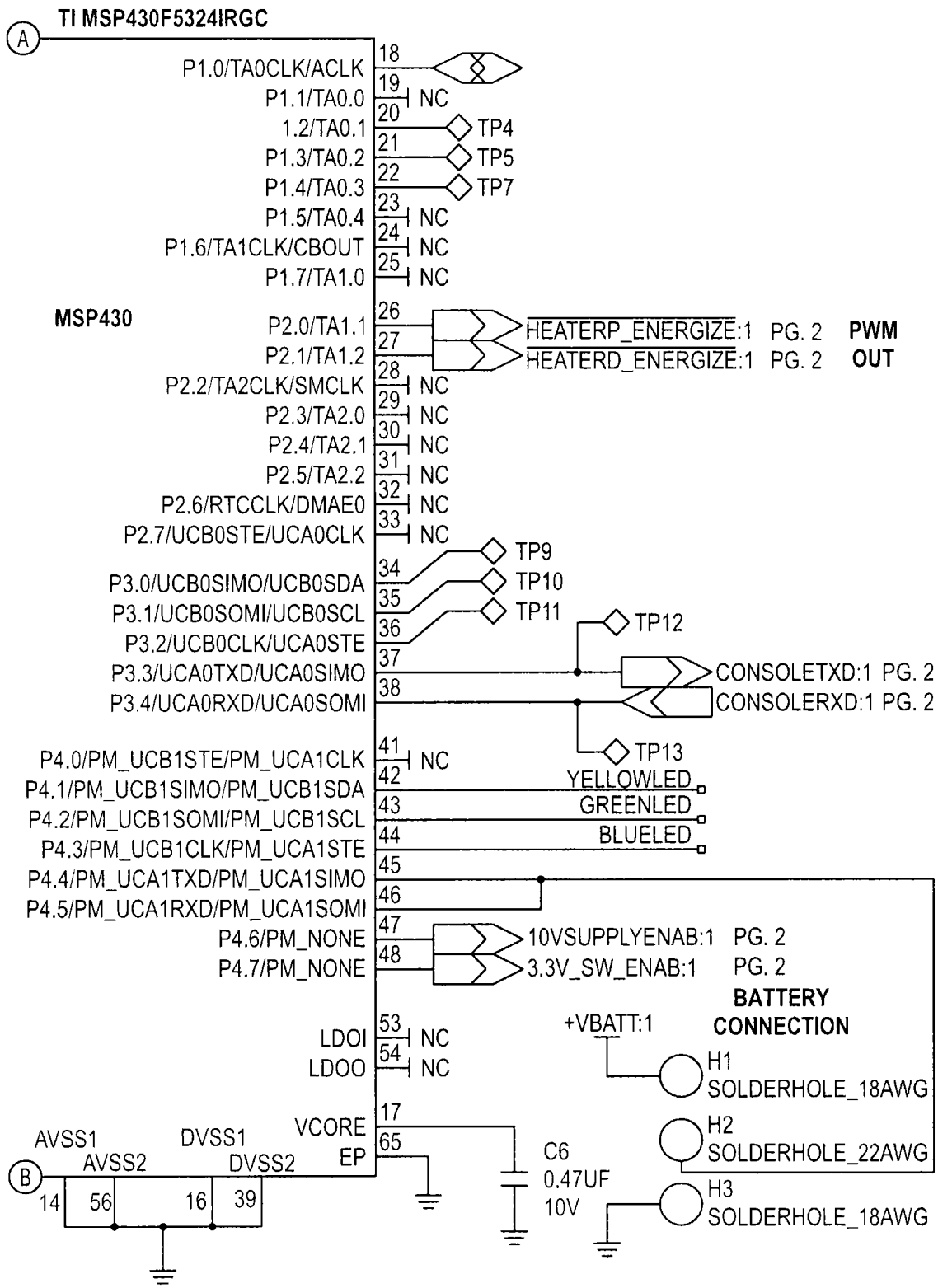
Figure 11D:
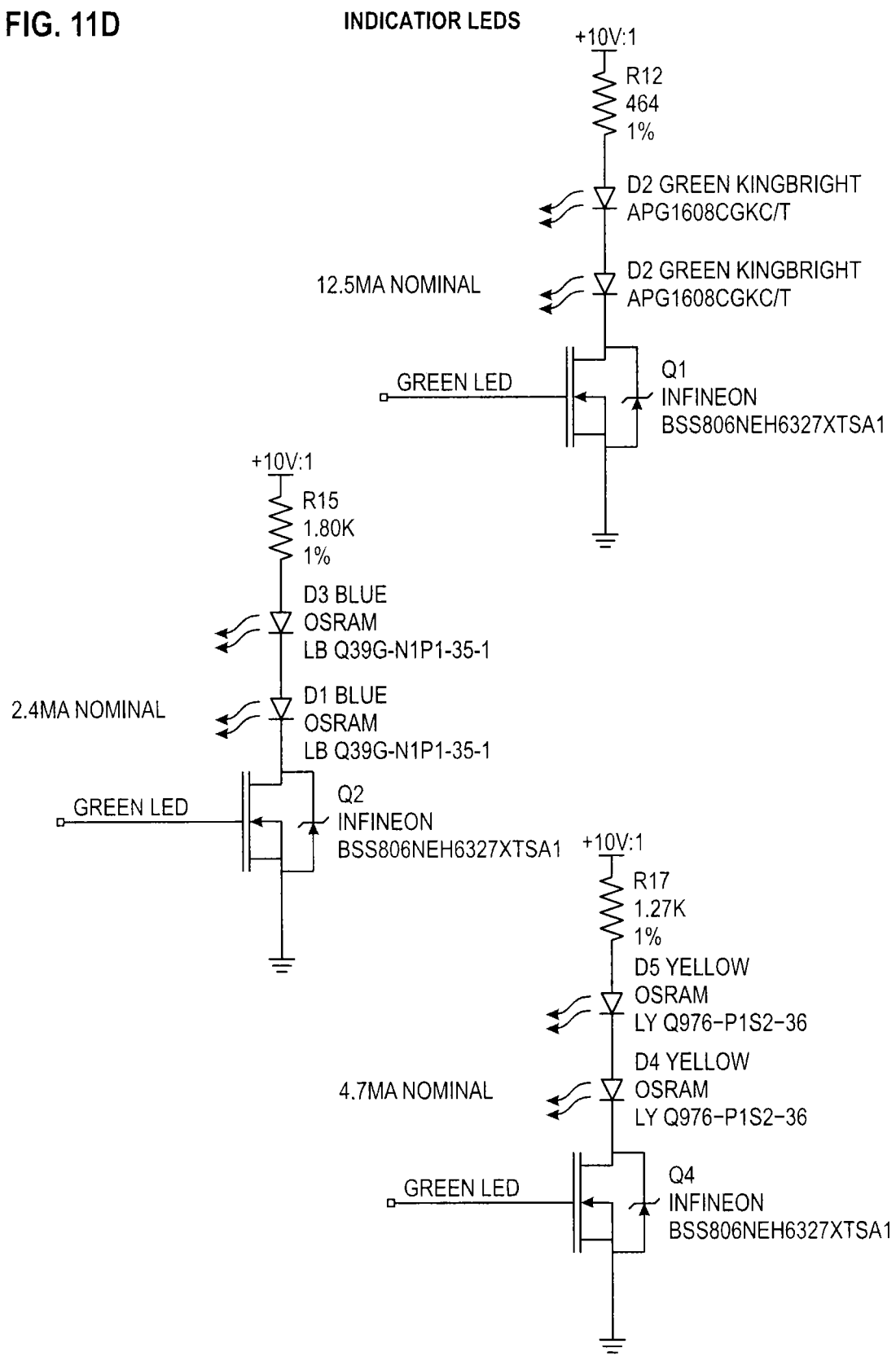

In some embodiments, the control unit 44 may include an output device 57 and an input device 58. The output device 57 of the control unit 44 may transmit information from the processor 50 to a user, such that the information may be perceived by the user. For example, but not by way of limitation, the output device 57 may be implemented as a server, a computer monitor, a cell phone, a tablet, a speaker, a website, a PDA, a fax, a printer, a projector, a laptop monitor, illumination devices, combinations thereof, and/or the like. For example, the output device 57 may include one or more illumination devices (e.g., LEDs) providing one or more status indicators (e.g., temperature reading, status of patient, status of infusion fluid 16, and/or the like). FIG. 5 illustrates the control unit 44 having a first output device 57*a* providing status indicators related to tubal segment 24*a* and a second output device 57*b* providing status indicators related to tubal segment 24*b*. In some embodiments, the output device 57 may be a cellular telephone wherein the control unit 44 communicates with a user's cellular telephone in providing status indicators, for example. FIG. 11D illustrates another exemplary embodiment wherein a status indicator system may include the use of indicator LEDs (e.g., green, blue and yellow). It should be noted that any number of indicators may be used to provide status indicators as needed. For example, a localized system using indicator LEDs may be provided, as well as, a communication to a cellular telephone and/or the like.

The input device 58 may transmit data to the processor 50 and may be implemented as a keyboard, a mouse, a touchscreen, a camera, a cellular phone, a tablet, a smart phone, a personal digital assistant (PDA), a microphone, a network adapter, a probe having a sensor therein, a microcapillary testing device or array, a microfluidic testing device, combination thereof, and the like.

In some embodiments, the control unit 44 may include a touch screen display forming the output device 57 and the input device 58. The touch screen display may be equipped with a graphical user interface (GUI) capable of communicating information to the user and receiving instructions from the user. Software stored on the one or more memories 52 of the control unit 44 may receive one or more commands (e.g., via the touch screen display) to provide activation of the control unit 44; processing of data according to a defined algorithm stored on the one or more memories 52, displaying received data and/or processed data, and/or monitoring system status and reporting fault conditions, for example.

The control unit 44 controls delivery of energy (e.g., electrical energy) from the power source 46 to the tubal segments 24*a* and 24*b*, and more particularly to the thermal element 30 of the tubal segments 24*a* and 24*b* shown in FIGS. 1A and 2. In some embodiments, the control unit 44 may control delivery of the energy via one or more channels 59. For example, in FIG. 5, the control unit 44 controls delivery of the energy via a first channel 59*a* to the tubal segment 24*a* and a second channel 59*b* to the tubal segment 24*b*. In some embodiments, the control unit 44 may automatically sense and/or determine the presence of infusion fluid 16 within the tubal body 18 such that the control unit 44 may begin delivery of the energy based on the presence of infusion fluid 16 within the tubal body 18 (e.g., without other external indicators such as an on/off switch).

The control unit 44 controls delivery of energy from the power source 46 to the tubal segments 24*a* and 24*b*. Referring to FIGS. 1A and 5, the power source 46 may provide energy to the control unit 44, the tubal segments 24*a* and 24*b*, and/or the sensors 48. In some embodiments, the power source 46 may be a battery and/or a power supply. For example, the power source 46 may include, but is not limited to, an integral or external AC/DC converter, primary batteries, rechargeable batteries, solar energy gathering device, an on/off switch, a voltage regulator and/or the like, for example. In some embodiments, the power source 46 may include a bridge such that a communications battery may connect to the power source 46 during field use. Further, in some embodiments, the power source 46 may further include a measurement system providing indications of status (e.g., low, fully charged). For example, FIG. 11C illustrates a battery measurement system for use in the control unit 14.

In some embodiments, the control unit 44 may control delivery of the energy to control the temperature of the infusion fluid 16 such that the temperature of the infusion fluid 16 is at a physiological beneficial temperature range, the temperature of the infusion fluid 16 is at a pre-set temperature range, the temperature of the infusion fluid 16 is based on a range of flow rates and/or ambient conditions, the temperature of the infusion fluid 16 is below a potentially detrimental temperature (e.g., temperature wherein hemolysis occurs), and/or the like, for example.

The control unit 44 utilizes sensing data from the sensors 48 to deliver the energy (e.g., electrical energy) to the tubal segments 24*a* and 24*b*. The sensors 48 may be positioned along the tubal body 18 to obtain and provide fluid measurements (e.g., temperature, flow) of the infusion fluid 16 flowing through the tubal body 18, and transmit such measurements to the control unit 44. In some embodiments, the sensors 48 may communicate the sensing data over one or more communication links 61 (e.g., single communication link, individual communication links or multiple communication links). The sensors 48 may communicate with the control unit 44 uni-laterally or bi-laterally. Transmission over the communication link 61 may be through a wired or wireless connection. The communication link may include one or more of the helical windings, either multiplexed with the thermal element 30, and/or an individual wind. The communication link may be formed of similar material or different material as the thermal element 30. In some embodiments, different conductive material may be selected to optimize performance and/or minimize manufacturing cost.

The sensors 48 may include, but are not limited to, thermistors, thermocouples, resistance temperature detectors (RTDs), flow sensors, pressure sensors, and/or other fluid or gas sensing elements capable of providing sensing data to the control unit 44. For example, in FIG. 11B, the control system 14 indicates the use of multiple thermistors.

In some embodiments, the sensors 48 may sense the flow rate of the infusion fluid 16 and display the flow rate to an operator of the thermic infusion system 10. In some embodiments, the control unit 44 may determine the flow rate using temperature sensing information provided across multiple sensors 48 and the amount of energy provided to the thermal elements 30, for example.

The one or more sensors 48 may be positioned within and/or adjacent to the tubal body 18. For example, FIGS. 1A, 1B and 5 illustrate three sensors 48a, 48b and 48c positioned within the tubal body 18. Although three sensors 48a, 48b and 48c are illustrated, any number of sensors 48 may be used.

Figure 6:
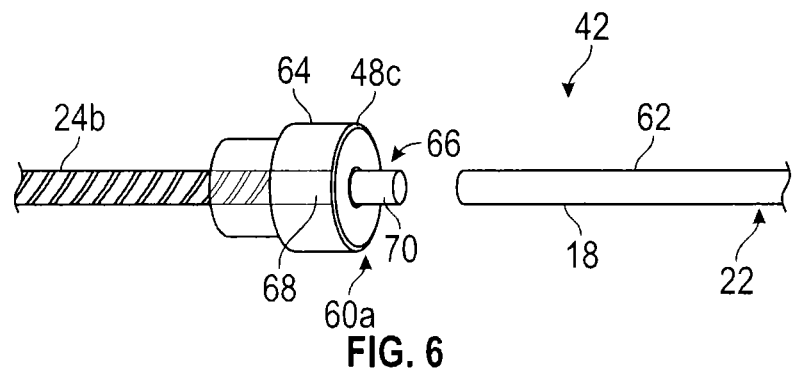
FIG. 6 is a perspective view of an exemplary coupler for use in the thermic infusion system of FIG. 1A.

In some embodiments, the sensors 48 may be integral within the tubal body 18. In some embodiments, one or more couplers 60 may be used to position the sensors 48 within the tubal body 18 such as the exemplary coupler 60a illustrated in FIG. 6. FIG. 6 illustrates the distal end 42 of the tubal body 18 in FIG. 1A, having the tubal segment 24b connecting to another portion 62 of the tubal body 18. The coupler 60a may include a housing 64 and a tubing connector 66. The housing 64 may be formed of materials including, but not limited to, polycarbonate, and/or the like. The sensor 48c may be contained within the housing 64 and positioned adjacent to the flow of the infusion fluid 16 such that the sensor 48c may sense temperature, flow, and/or the like of the infusion fluid 16. The housing 64 is illustrated in FIG. 6 as cylindrical, however, the housing 64 may be any shape including, but not limited to rectangular, square, oval and/or any fanciful shape.

Figure 10:
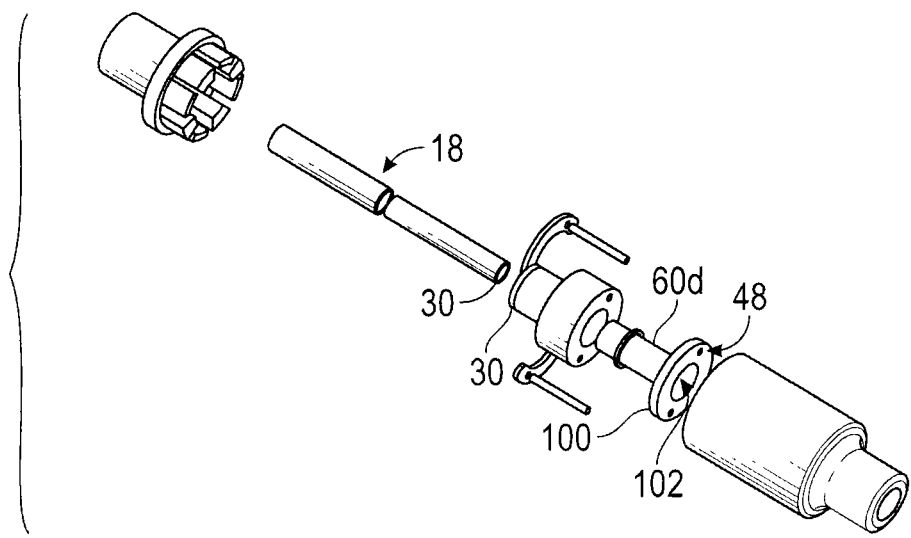
FIG. 10 illustrates an exploded view of an exemplary thermal element in communication with a printed circuit board (PCB) for use in the thermic infusion system of FIG. 1A.

In some embodiments, the sensor 48 may be positioned on a printed circuit board (PCB), wherein the body of the sensor 48 may be positioned in contact with traces that contact a thermally conductive coupler in the tubal body 18 providing for thermal conductivity between the sensor 48 and the infusion fluid 16. For example, FIG. 10 illustrates an exemplary embodiment of a sensor 48 positioned in communication with a PCB 100. In this example, the material of the PCB 100 may minimize thermal conductivity to the thermal elements 30 and/or the tubal body 18 while providing electrical communication and/or connection to the control unit 44 (shown in FIG. 1A) while remaining electrically insulated from the infusion fluid 16 (shown in FIG. 1A). For example, an inner lining 102 of the PCB 100 may be in thermal communication with the sensor 48. In some embodiments, the PCB 100 may have separate traces for thermal conductivity and electrical conductivity. Additionally, the coupler 60d, or a portion of the coupler 60d may be formed of conductive material.

The tubing connector 66 may be configured to connect to the tubal segment 24b and the portion 62 of the tubal body 18. Connection of the tubing connector 66 to the portion 62 of the tubal body 18 may be configured to ensure flow of the infusion fluid 16 therethrough. In some embodiments, the tubing connector 66 may be positioned such that a portion 68 of the tubing connector 66 is within the housing 64 and a portion of the tubing connector 66 is positioned external to the housing 64 as illustrated in FIG. 6. In some embodiments, a polymer or polymer-type mold may be formed to surround the coupler 60a to ease the connection for a user and/or stabilize the connection. As one skilled in the art will appreciate, a similar coupler 60a may also be used to connect a portion 72 of the tubal body 18 to the tubal segment 24a illustrated in FIG. 1A.

Figure 7:
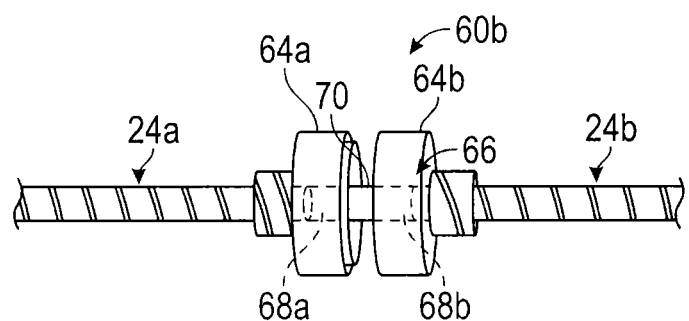
FIG. 7 is a perspective view of another exemplary coupler for use in the thermic infusion system of FIG. 1A.

FIG. 7 illustrates another exemplary embodiment of a coupler 60b. The coupler 60b may include a first housing 64a and a second housing 64b connected via the tubing connector 66. A portion 68a of the tubing connector 66 may be positioned within the first housing 64a and a portion 68b of the tubing connector 66 may be positioned within the second housing 64b such that between the first housing 64a and the second housing 64b a portion 70 is external of each of the first housing 64a and the second housing 64b.

Figure 8:
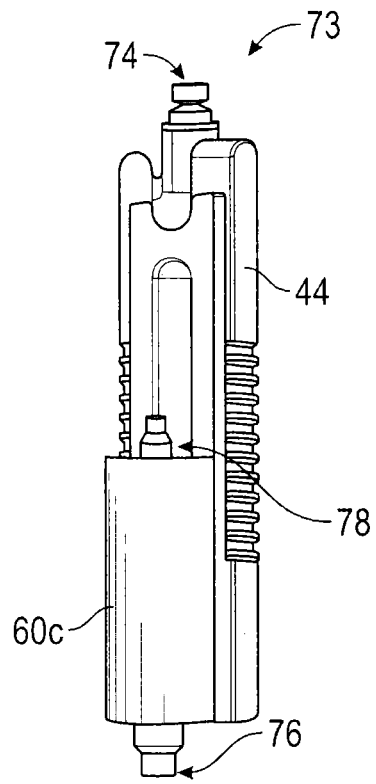
FIG. 8 is a perspective view of an exemplary housing for a control unit for use in the thermic infusion system of FIG. 1A.

FIG. 8 illustrates an exemplary embodiment of a housing 73 for the control unit 44. The housing 73 is illustrated as rectangular, however, the housing 73 may be any shape including, but not limited to, square, oval, cylindrical, and/or any fanciful shape which may, in certain embodiments, reflect the type of infusate for which the control unit is to be used (e.g., the shape of a drop of blood). The housing 73 may include a port 74 for connecting to the power source 46 shown in FIG. 1A. In some embodiments, the housing 73 for the control unit 44 may be positioned adjacent to the coupler 60c as illustrated in FIG. 8. The coupler 60c may include an inflow port 76 and an outflow port 78. In some embodiments, the elements of the coupler 60b illustrated in FIG. 7 may be housed within the coupler 60c.

Figure 9:
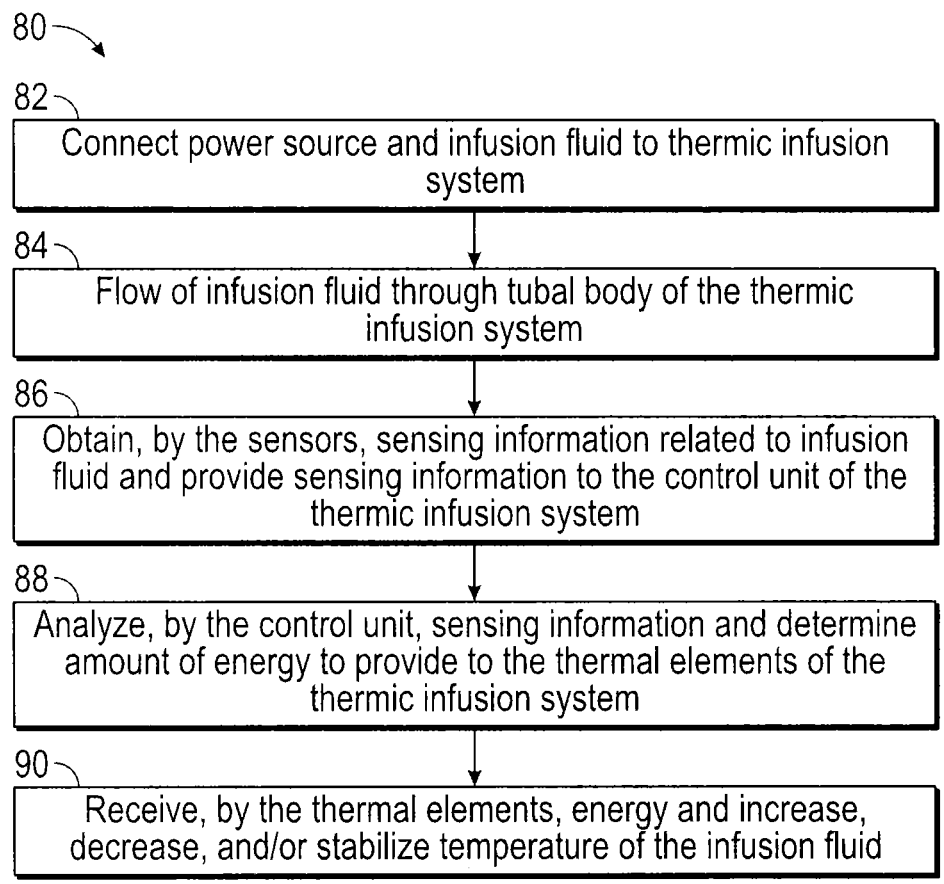
FIG. 9 is a flow chart of an exemplary method for using the thermic infusion system of FIG. 1A.

FIG. 9 illustrates a flow chart 80 of an exemplary method for using the thermic infusion system 10. In a step 82, the power source 46 and the infusion fluid 16 may be connected to the thermic infusion system 10. In a step 84, the infusion fluid 16 may flow through the tubal body 18 of the thermic infusion system 10. In a step 86, one or more sensors 48 may obtain sensing information (e.g., temperature) related to the infusion fluid 16 and provide the sensing information to the control unit 44. In a step 88, the control unit 44 may analyze the sensing information and determine the amount of energy (e.g., electrical energy) to provide to the tubal segments 24a and 24b, and more particularly, to the thermal elements 30 of the tubal segments 24a and 24b. Each tubal segment 24a and 24b may receive different amounts of energy (e.g., electrical energy). For example, the tubal segment 24a may receive a greater amount of electrical energy to provide more heat to the infusion fluid 16 as compared to the amount of electrical energy provided to the tubal segment 24b as may the converse be true in an alternate embodiment. In a step 90, the thermal elements 30 may receive electrical energy and increase, decrease and/or stabilize the temperature of the infusion fluid 16. It should be noted that the control unit 44 may also signal the delivery of electrical energy to the tubal segments 24a and 24b prior to flow of the infusion fluid 16 through the tubal body 18, such that thermal regulation of the infusion fluid 16 may occur immediately upon flow of the infusion fluid 16 through the tubal body 18.

In some embodiments, the thermic infusion system 10 may be included within a kit. The kit may include one or more thermic infusions systems 10 and one or more power sources 46. Additionally, in some embodiments, the kit may include one or more bags of infusion fluid 16. To aid in use, the kit may include a quick start guide, a jump drive having video and/or text instruction, a written evaluation tool, and/or the like. The kit may be housed in a protective housing, for example.

It should be noted that the thermic infusion system 10 may be used and/or included within other systems known within the art. For example, the thermic infusion system 10 may be used in heating for a dialysis system, chemotherapy system, blood exchange system, and/or the like. Further, one or more elements of the thermic infusion system 10 may be included within other systems known within the art.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A thermic infusion system, comprising:
   a first tubal segment having a first inner sheath defining a first hollow cylindrical body for conveying infusion fluid therethrough;
   a first outer sheath disposed around the first inner sheath;
   a first thermal element positioned between the first inner sheath and the first outer sheath and configured to convert electrical energy into heat for heating or cooling the conveyed infusion fluid in the first hollow cylindrical body;
   a second tubal segment in series fluid communication with the first tubal segment, having a second inner sheath defining a second hollow cylindrical body for conveying the infusion fluid therethrough received from the first tubal segment;
   a second outer sheath disposed around the second inner sheath;
   a second thermal element positioned between the second inner sheath and the second outer sheath and configured to convert electrical energy into heat for heating or cooling the conveyed infusion fluid in the second hollow cylindrical body;
   a control unit;
   a printed circuit board assembly; and
   at least one temperature sensor positioned on the printed circuit board assembly and configured to provide temperature sensing information to the control unit,
   wherein a material of the printed circuit board assembly minimizes thermal conductivity to the at least one temperature sensor from the first thermal element and from the second thermal element, wherein the material further provides electrical insulation between the at least one temperature sensor and the conveyed infusion fluid, wherein the printed circuit board assembly comprises an inner lining configured to provide thermal conductivity between the at least one temperature sensor and at least one of the first hollow cylindrical body and the second hollow cylindrical body, wherein the control unit is configured to regulate different electrical energy amounts provided to the first thermal element and to the second thermal element based on the temperature sensing information, and wherein the first hollow cylindrical body and the second hollow cylindrical body essentially consist of geometric changes which limit shear force in laminar fluid flow to less than 10 Pa on the infusion fluid conveyed therethrough.

2. The thermic infusion system of claim 1, wherein the control unit is further configured to provide more electrical energy to the first thermal element than to the second thermal element.

3. The thermic infusion system of claim 1 wherein the first tubal segment is longer than the second tubal segment.

4. The thermic infusion system of claim 1, wherein the first thermal element is formed in a helical shape wrapping around the first inner sheath.

5. The thermic infusion system of claim 4, wherein the first thermal element has a pitch of approximately 6.3 mm per revolution.

6. The thermic infusion system of claim 1, wherein the first inner sheath comprises a more rigid material than a material which the first outer sheath comprises.

7. The thermic infusion system of claim 1, further comprising at least one communication link configured to communicate the temperature sensing information to the control unit.

8. The thermic infusion system of claim 7, wherein the at least one communication link is positioned between the first inner sheath and the first outer sheath.

9. The thermic infusion system of claim 1, wherein the first inner sheath and the first outer sheath are configured to rebound from kinking.

10. The thermic infusion system of claim 1, wherein the first inner sheath and the first outer sheath are configured to rebound from crushing.

11. The thermic infusion system of claim 1, wherein the second inner sheath and the second outer sheath are configured to rebound upon at least one of kinking or crushing.

12. The thermic infusion system of claim 1, wherein the at least one temperature sensor comprises at least two temperature sensors, and wherein the control unit is further configured to determine a flow rate of the conveyed infusion fluid using a difference in temperature between the at least two temperature sensors.

13. The thermic infusion system of claim 1, wherein one or more of the first and second tubal segments have a Reynolds Number within approximately 300 to 600.

14. A thermic infusion system, comprising:
   a tubal segment having an inner sheath defining a hollow cylindrical body for conveying infusion fluid therethrough;
   an outer sheath disposed around the inner sheath;
   a thermal element positioned between the inner sheath and the outer sheath and configured to convert electrical energy into heat for heating or cooling the conveyed infusion fluid in the hollow cylindrical body;
   a control unit; and
   at least one distal temperature sensor positioned at a distal end of the thermal element, wherein the at least one distal temperature sensor is provided with a thermally conductive material between the at least one distal temperature sensor and the hollow cylindrical body of the tubal segment, and configured to provide distal temperature sensing information to the control unit; and
   at least one proximal temperature sensor positioned at a proximal end of the thermal element, provided with a thermally conductive material between the at least one proximal temperature sensor and the hollow cylindrical body of the tubal segment, and configured to provide proximal temperature sensing information to the control unit;

wherein the control unit is configured to receive the distal temperature sensing information, and to regulate different electrical energy amounts provided to the thermal element based on the received temperature sensing information, and wherein the hollow cylindrical body essentially consists of geometric changes which limit shear force in laminar fluid flow to less than 10 Pa on the infusion fluid conveyed therethrough.

15. The thermic infusion system of claim 14, wherein the tubal segment has a Reynolds Number within approximately 300 to 600.

16. A method of using a thermic infusion system, comprising the steps of:

connecting a power source and an infusion fluid source to a thermic infusion system such that an infusion fluid from the infusion fluid source flows through a tubal body of the thermic infusion system, the thermic infusion system comprising:

at least one tubal segment having an inner sheath defining a hollow cylindrical body for conveying the infusion fluid therethrough;

an outer sheath disposed around the inner sheath;

a thermal element positioned between the inner sheath and the outer sheath and configured to convert electrical energy into heating or cooling of the conveyed infusion fluid in the hollow cylindrical body;

a control unit;

at least one distal temperature sensor positioned at a distal end of the thermal element, wherein the at least one distal temperature sensor is provided with a thermally conductive material between the at least one distal temperature sensor and the hollow cylindrical body of the at least one tubal segment, and configured to provide distal temperature sensing information to the control unit; and at least one proximal temperature sensor positioned at a proximal end of the thermal element, provided with a thermally conductive material between the at least one proximal temperature sensor and the hollow cylindrical body of the tubal segment, and configured to provide proximal temperature sensing information to the control unit;

wherein the control unit is configured to receive the distal temperature sensing information, and to regulate different electrical energy amounts provided to the thermal element based on the received temperature sensing information, and wherein the hollow cylindrical body essentially consists of geometric changes which limit shear force in laminar fluid flow to less than 10 Pa on the infusion fluid conveyed therethrough.

17. The method of claim 16, wherein the thermic infusion system includes at least a second tubal segment.

* * * * *